United States Patent [19]

Krantz et al.

[11] Patent Number: 4,668,703

[45] Date of Patent: May 26, 1987

[54] γ-ALLENYL-γ-AMINOBUTYRIC ACIDS

[75] Inventors: Alexander Krantz, Toronto; Arlindo L. Castelhano; Diana H. Pliura, both of Mississauga, all of Canada

[73] Assignee: Syntex (U.S.A.) Inc., Palo Alto, Calif.

[21] Appl. No.: 750,829

[22] Filed: Jul. 1, 1985

Related U.S. Application Data

[63] Continuation-in-part of Ser. No. 511,691, Jul. 7, 1983, abandoned.

[51] Int. Cl.[4] ................. C07C 101/28; A61K 31/195
[52] U.S. Cl. ..................... 514/549; 260/401; 260/402.5; 260/404; 260/404.5; 260/501.19; 514/478; 514/485; 514/539; 514/542; 514/534; 514/561; 514/562; 514/563; 514/616; 514/618; 514/620; 514/626; 546/216; 546/243; 548/543; 548/551; 560/9; 560/12; 560/13; 560/27; 560/29; 560/24; 560/30; 560/38; 560/39; 560/41; 560/157; 560/159; 560/161; 560/169; 560/172; 562/426; 562/430; 562/443; 562/444; 562/448; 562/449; 562/450; 562/561; 562/574; 564/154; 564/155; 564/158; 564/152; 564/159; 564/162; 564/164; 564/165; 564/215

[58] Field of Search ............... 260/402.5, 401, 404, 260/404.5, 501.19; 560/9, 12, 13, 24, 27, 29, 30, 38, 39, 41, 157, 159, 161, 169, 172; 562/426, 430, 443, 444, 448, 449, 450, 561, 574; 564/152, 154, 155, 159, 162, 164, 165; 514/478, 534, 542, 949

[56] References Cited

U.S. PATENT DOCUMENTS

| | | | |
|---|---|---|---|
| 3,959,356 | 5/1976 | Metcalf | 562/574 |
| 3,960,927 | 6/1976 | Metcalf | 560/38 |
| 4,104,305 | 8/1978 | Inamoto | 260/501.21 |
| 4,178,463 | 12/1979 | Gittos et al. | 562/574 |
| 4,326,071 | 4/1982 | Bey | 562/574 |
| 4,454,156 | 6/1984 | Cassara | 562/574 |
| 4,454,157 | 6/1984 | Swallow | 260/507.21 |

FOREIGN PATENT DOCUMENTS 0094886  11/1983  European Pat. Off. .
2607620   9/1976  Fed. Rep. of Germany .

OTHER PUBLICATIONS

J. Chem. Soc. Perkin Trans. I, 1984.
Org. Synthesis, 1985, vol. 63, pp. 203–205.
Tetrahedron Letters vol. 21, pp. 929–930.
J.C.S. Chem. Comm. 1979, pp. 859–860.

*Primary Examiner*—Michael L. Shippen
*Attorney, Agent, or Firm*—Liza K. Toth; Tom M. Moran

[57] ABSTRACT

This invention is for γ-allenyl-γ-aminobutyric acid derivatives which are γ-aminobutyric acid transaminase inhibitors.

20 Claims, No Drawings

γ-ALLENYL-γ-AMINOBUTYRIC ACIDS

This application is a continuation-in-part of a presently copending application U.S. Ser. No. 511,691 filed July 7, 1983, now abandoned.

BACKGROUND OF THE INVENTION

This invention relates to γ-allenic-substituted amino acids and in particular, γ-aminobutyric acid.

A number of studies have demonstrated that γ-aminobutyric acid is a major inhibitory transmitter of the central nervous system (i.e. Y. Godin, et. al. Journal of Neurochemistry, 16, 869 (1969)). A perturbation of the excitation and inhibition interplay can lead to disease states such as Huntington's chorea, Parkinsonism, schizophrenia, epilepsy, depression, hyperkinesis and manic depressive disorders [Biochem. Pharmacol., 23, 2367-2649 (1974)]. A number of compounds, most notably γ-monofluoromethyl-γ-aminobutyric acid, γ-acetylenic and γ-vinyl-γ-aminobutyric acid are potent irreversible inhibitors of γ-aminobutyric acid transaminase and significantly increase the brain level of γ-aminobutyric acid in animals rendering them useful in the treatment of the aforementioned disease states.

It has been found that γ-allenyl-γ-aminobutyric acid derivatives are potent inhibitors of γ-aminobutyric acid transaminase.

SUMMARY OF THE INVENTION

The novel compounds of this invention have the formula:

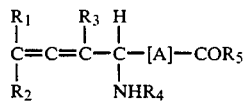
(I)

and the pharmaceutically acceptable salts thereof wherein:

$R_1$ is hydrogen, halo, alkyl of 1 to 4 carbons, alkyl phenyl of 7 to 9 carbon atoms or substituted phenyl or alkyl phenyl of 7 to 9 carbon atoms wherein the substituents are halo, alkyl or 1 to 4 carbon atoms, alkoxy of 1 to 4 carbon atoms, thioalkyl of 1 to 4 carbon atoms or amino alkyl of 1 to 4 carbon atoms, or sulfonyl- or sulfoxylalkyl of 1 to 4 carbon atoms, sulfonyl- or sulfoxylaryl, or sulfonyl- or sulfoxylhaloalkyl of 1 to 4 carbon atoms;

$R_2$ and $R_3$ are independently hydrogen, halo, alkyl of 1 to 4 carbons, alkyl phenyl of 7 to 9 carbon atoms or substituted phenyl or alkyl phenyl of 7 to 9 carbon atoms wherein the substituents are halo, alkyl of 1 to 4 carbon atoms, alkoxy of 1 to 4 carbon atoms, thioalkyl of 1 to 4 carbon atoms, or amino alkyl of 1 to 4 carbon atoms;

$R_4$ is hydrogen, alkyl carbonyl wherein the alkyl moiety contains from 1 to 22 carbon atoms, alkoxy carbonyl wherein the alkoxy moiety contains from 1 to 22 carbon atoms or Formula II

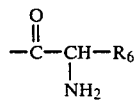
(II)

wherein $R_6$ is hydrogen, alkyl of 1 to 4 carbon atoms, benzyl or p-hydroxybenzyl;

$R_5$ is hydroxyl, alkoxy of 1 to 22 carbons, alkyl amino of 1 to 22 carbon atoms or Formula III

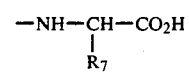
(III)

wherein $R_7$ is hydrogen, alkyl of 1 to 4 carbon atoms, benzyl or p-hydroxybenzyl;

A is —CH=CH— or Formula IV

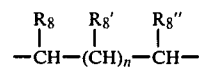
(IV)

wherein $R_8$, $R_8'$ and $R_8''$ are independently hydrogen, alkyl of 1 to 4 carbon atoms, phenyl or substituted phenyl wherein the substituents are halo or alkoxy of 1 to 4 carbon atoms and n is the integer 0 or 1.

In a second aspect, this invention covers the lactams of Formula I, represented by Formula IA which is

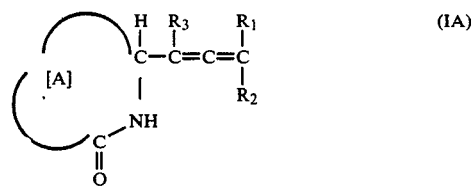
(IA)

wherein $R_1$, $R_2$, $R_3$ and [A] are the same as defined herein above.

In another aspect this invention relates to a pharmaceutical composition comprising a compound of Formula I or a pharmaceutically acceptable salt thereof in combination with a pharmaceutically acceptable excipient. In yet another aspect this invention is drawn to a method for inhibiting γ-aminobutyric acid transaminase, which method comprises administering to a mammal an effective amount of a compound according to Formula I or a pharmaceutically acceptable salt thereof either alone or in admixture with a pharmaceutical excipient.

In yet another aspect this invention relates to a process for preparing a compound of Formula I which process comprises:

a. hydrolyzing a compound of Formula (IA)

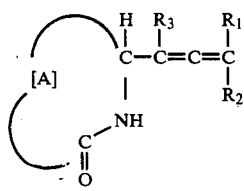
(IA)

wherein $R_1$, $R_2$, $R_3$ and [A] are defined herein above with acid; or b. esterifying the free acid of the compound of Formula I wherein $R_5$ is hydroxyl; or c. amidizing a compound of Formula I wherein $R_5$ is hydroxyl; or d. amidizing a compound of Formula I wherein $R_4$ is hydrogen; or e. converting the free base of the compound of Formulas I with an acid to a pharmaceutically acceptable acid addition salt; or f. converting the free acid of the compound of Formula I with a base to a pharmaceutically acceptable acid salt; or g. converting an acid salt with a base to the corresponding free acid; or h. converting an acid addition salt with a base to the corresponding free base; or i. converting an ester to the free acid with an acid or to the corresponding pharmaceutically acceptable salt with a base; or j. converting an amide to the amine with a base or to the acid addition salt with an acid.

The preferred compounds of this invention are those wherein $R_1$, $R_2$ and $R_3$ are independently hydrogen or alkyl of 1 to 4 carbon atoms and $R_5$ is hydroxyl or an acyl radical of 1 to 22 carbon atoms. More preferred are those compounds wherein $R_1$, $R_2$ and $R_3$ are hydrogen, or wherein $R_1$, $R_2$ and $R_3$ are independently hydrogen or methyl. Most particularly preferred are;

4-amino-5,6-heptadienoic acid;
4-amino-5-methyl-5,6-heptadienoic acid; and
4-amino-5,6-octadienoic acid.

DESCRIPTION OF THE INVENTION

The compounds of this invention are useful in inhibiting the enzyme γ-aminobutyric acid transaminase. As such these compounds increase the level of γ-aminobutyric acid (GABA) in the body generally. But more importantly, these compounds will increase the level of GABA in the mammalian brain making the compounds useful for treating a number of diseases associated with lowered GABA levels in the brain such as Huntington's chorea, Parkinsonism, schizophrenia, epilepsy, depression, hyperkinesis and manic depressive disorders. For a review of the pharmacological effects of GABA transaminase inhibitors see Metcalf, B. W., *Biochem. Pharm.* 28, 1705 (1979) and Loscher, W., *Arch. Int. Pharmacodyn.*, 257, 32, (1982). As GABA transaminase inhibitors, these compounds are also useful for treating parasitic infections, for example helminthic and protozoal infections, see Wang, C. C., *TIBS*, 354 (1982).

The term "halo" refers to fluoro, chloro, bromo and iodo.

Alkylcarbonyl of 1 to 4 carbon atoms refers to a straight or branched carbon chain containing a carbonyl group which forms an amide with the nitrogen.

Alkoxycarbonyl groups having 1 to 22 carbons refer to a straight or branched carbon chain attached to the ether oxygen of an ester function.

An alkyl group of one to four carbon atoms encompasses both straight and branched alkane radicals such as methyl, ethyl, n-propyl, isopropyl, n-butyl, isobutyl, t-butyl and sec-butyl.

Alkoxy carries the conventional definition, herein having up to 22 carbon atoms either straight or branched and exemplified by the following: methoxy, ethoxy, propoxy, isopropoxy, n-butoxy, t-butoxy, n-pentoxy, n-hexyloxy, n-heptyloxy, n-octyloxy or the like.

Phenyl alkyl of 7 to 9 carbon atoms refers to benzyl, phenethyl, and phenylpropyl. The phenyl ring may be substituted with one or more of the same or different substituents such as halo, alkyl of 1 to 4 carbons, alkoxy of 1 to 4 carbons, thioalkyl wherein alkyl comprises 1 to 4 carbons or monoalkylamino where again the alkyl moiety has 1 to 4 carbons. Up to five substituents may be present on the ring. However it is preferred to have 1 to 3 substituents. While the substituent pattern may be a mixture of substituents, it is preferred to have multiple substituents be the same, for example 1,4,6-trichlorobenzyl or 1,4,6-trimethylphenethyl.

The compounds of this invention have at least one asymmetric carbon, the N-bearing carbon of Formula I and IA. Additionally, certain other carbons of the intermediate structures necessary for preparing these compounds may be asymmetric depending on the particular intermediate. This invention is intended to cover all optical isomers, whether they exist as a d,l mixture or after they have been resolved into their respective antipodes. Unless otherwise specified, the intermediates and the compounds of Formula I and IA will be a mixture of the d,l isomers.

If desired, the compounds herein may be resolved into their optical antipodes by conventional resolution means; for example by separation (e.g. fractional crystallization) of the diastereomeric salts formed by the reaction of these compounds with optically active acids. Exemplary of such optically active acids are the optically active forms of camphor-10-sulfonic acid, 2-bromo-camphor-10-sulfonic acid, camphoric acid, menthoxyacetic acid, tartaric acid, malic acid, diacetyltartaric acid, pyrrolidine-5-carboxylic acid and the like. The separated pure diastereomeric salts may then be cleaved by standard means to afford the respective optical isomers of the compounds of Formula I.

Where $R_1$, $R_2$ and $R_3$ are dissimilar, the compounds may exist as diastereomers. It is intended that mixtures of stereoisomers and the individual isomers be covered by this invention.

Administration of the active compounds and salts described herein can be via any of the accepted modes of administration for agents which are transaminase inhibitors. These methods include oral, parenteral and otherwise systemic or aerosol forms.

Depending on the intended mode of administration, the compositions used may be in the form of solid, semi-solid or liquid dosage forms, such as, for example, tablets, suppositories, pills, capsules, powders, liquids, suspensions, or the like, preferably in unit dosage forms suitable for single administration of precise dosages. The compositions will include a conventional pharmaceutical carrier or excipient and an active compound of Formula I or the pharmaceutically acceptable salts thereof and, in addition, may include other medicinal agents, pharmaceutical agents, carriers, adjuvants, etc.

For general methods for making esters, amides, carbamates, salts and peptides of amino acids, see J. P. Greenstein and M. Winitz, "Chemistry of the Amino Acids", John Wiley, Vol. 1-3, 1961.

Pharmaceutically acceptable acid addition salt refers to those salts which retain the biological effectiveness and properties of the free bases and which are not biologically or otherwise undesirable, formed with inorganic acids such as hydrochloric acid, hydrobromic acid, sulfuric acid, nitric acid, phosphoric acid and the like, and organic acids such as acetic acid, propionic acid, glycolic acid, pyruvic acid, oxalic acid, malic acid, malonic acid, succinic acid, maleic acid, fumaric acid, tartaric acid, citric acid, benzoic acid, cinnamic acid, mandelic acid, methanesulfonic acid, ethanesulfonic acid, p-toluenesulfonic acid, salicylic acid and the like.

The compounds of Formula I in free base form may be converted to the acid addition salts by treating the free base with a stoichiometric excess of the appropriate organic or inorganic acid, such as, for example, phosphoric, pyruvic, hydrochloric or sulfuric acid and the like. Typically, the free base is dissolved in a polar organic solvent such as ethanol or methanol, and the acid added thereto. The temperature is maintained between about 0° C. to 100° C. The resulting acid addition salt precipitates spontaneously or may be brought out of solution with a less polar solvent.

The acid addition salts of the compounds of Formula I may be decomposed to the corresponding free base by treating with a stoichiometric excess of a suitable base, such as potassium carbonate or sodium hydroxide, typically in the presence of aqueous solvent, and at a temperature of between about 0° C. and 100° C. The free base form is isolated by conventional means, such as extraction with an organic solvent.

Salts of the compounds of Formula I may be interchanged by taking advantage of differential solubilities of the salts, volatilities or acidities of the acids, or by treating with the appropriately loaded ion exchange resin. For example, the interchange is effected by the reaction of a salt of the compounds of formula I with a sllight stoichiometric excess of an acid of a lower pKa than the acid component of the starting salt. This conversion is carried out at a temperature between about 0° C. and the boiling point of the solvent being used as the medium for the procedure.

The salt derivatives of the compounds of Formula I and IA are prepared by treating the corresponding free acids of the compounds of Formula I with at least one molar equivalent of a pharmaceutically acceptable base. Representative pharmaceutically acceptable bases are sodium hydroxide, potassium hydroxide, ammonium hydroxide, calcium hydroxide, trimethylamine, lysine, caffeine, and the like. The reaction is conducted in water, alone or in combination with an inert, water-miscible organic solvent, at a temperature of from about 0° C. to about 100° C., preferably at room temperature. Typical inert, water-miscible organic solvents include methanol, ethanol, or dioxane. The molar ratio of compounds of Formula I to base used are chosen to provide the ratio desired for any particular salt.

Salts derived from inorganic bases include sodium, potassium, lithium, ammonium, calcium, magnesium, ferrous, zinc, copper, manganous, aluminum, ferric, manganic salts and the like. Particularly preferred are the ammonium, potassium, sodium, calcium, and magnesium salts. Salts derived from pharmaceutically acceptable organic non-toxic bases include salts of primary, secondary, and tertiary amines, substituted amines including naturally occurring substituted amines, cyclic amines and basic ion exchange resins, such as isopropylamine, trimethylamine, diethylamine, triethylamine, tripropylamine, ethanolamine, 2-dimethylaminoethanol, 2-diethylaminoethanol, tromethamine, dicyclohexylamine, lysine, arginine, histidine, caffeine, procaine, hydrabamine, choline, betaine, ethylenediamine, glucosamine, methylglucamine, theobromine, purines, piperazine, piperidine, N-ethylpiperidine, polyamine resins and the like. Particularly preferred organic non-toxic bases are isopropylamine, diethylamine, ethanolamine, tromethamine, dicyclohexylamine, choline and caffeine.

PREPARATIONS AND EXAMPLES

The compounds of this invention can be readily made by at least two procedures. In the first procedure, succinimide or an analog is reacted with a β-hydroxy acetylene compound using the procedure of O. Mitsunobu, M. Wada and T. Sano, J.A.C.S., 94, 679, 1972. This resulting N-substituted succinimide, or an analog, is then treated with a reducing agent such as sodium borohydride to give a 5-hydroxy-2-pyrrolidone compound. The procedure of A. R. Chamberlin and J. Y. L. Chung, Tet. Lett., 23, 2619, 1982 is preferred. A rearrangement of the acetylene group is then effected by means of a Aza-Cope rearrangement under the conditions described by D. J. Hart and T. K. Yang, ibid, 23, 2761, 1982 and P. M. M. Nossin, J. A. M. Hamersima, and W. N. Speckamp, Tet. Lett., 23, 3807, 1982. The pyrrolidone ring is then opened by dilute acid under an inert atmosphere under reflux conditions, for example, dilute HCl under argon at reflux for 2 or more days.

In the second procedure, a 1,5-diacyl-2-pyrrolidone is prepared from glutamic acid, an alkyl or aryl anhydride, 4-dimethylaminopyridine, and triethylamine according to the method of Steglich (W. Steglich, et al., Liebigs, Ann. Chem., 1753, 1974). The lithium salt of trimethylsilylacetylene or an appropriate analog thereof is reacted with the 1,5-diacyl-2-pyrrolidone under dry, inert atmosphere conditions at reduced temperature in an inert solvent by addition of the pyrrolidone to a preformed lithium trimethylsilylacetylide salt solution. Removal of the trimethylsilyl group is effected at room temperature by the addition of a base such as sodium hydroxide. Rearrangement of the acetylene group to give the substituted allenyl is done according to the method of P. Baret, E. Barreins, A. E. Greene, J. L. Luche, M. A. Teixeira, and P. Crabbe, Tetrahedron, 35, 2931, (1979). The pyrrolidone ring is then opened inthe same manner as described above for the first procedure.

Schematically, preparation of the compounds of this invention may be carried out as follows.

Reaction Scheme I outlines a process for preparing compounds of this invention.

REACTION SCHEME I

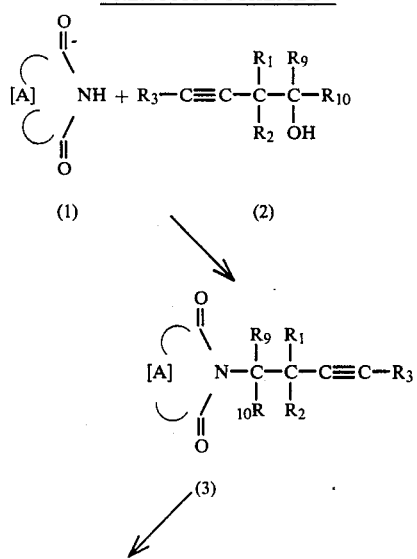

-continued
REACTION SCHEME I

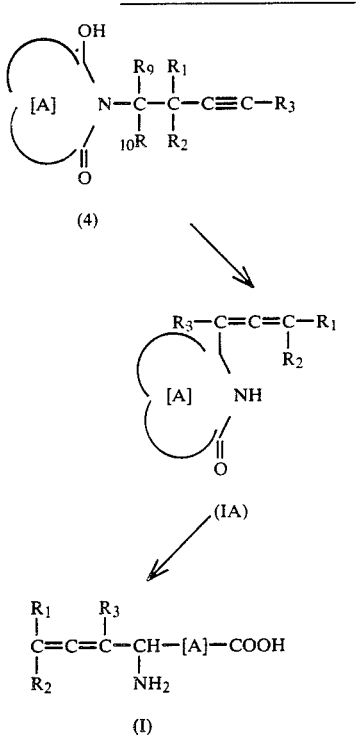

The substituents $R_9$ and $R_{10}$ may be independently hydrogen, alkyl or benzyl.

Reaction Scheme II illustrates an alternative method for making the compounds of this invention.

REACTION SCHEME II

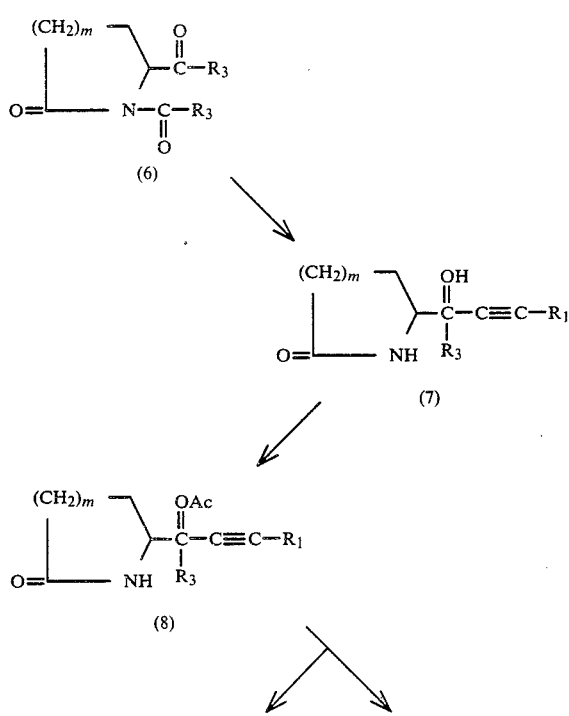

-continued
REACTION SCHEME II

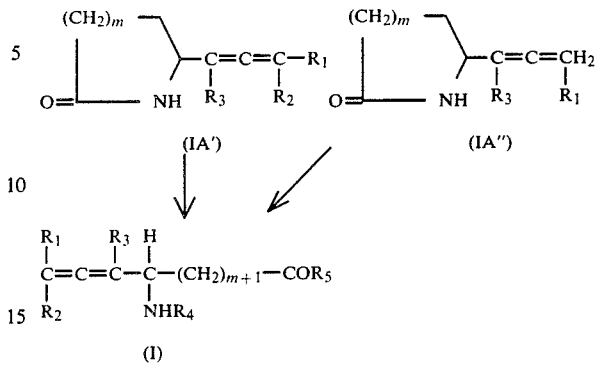

In the foregoing formulas in Scheme II, $R_1$ and $R_2$ are defined herein above, $R_3$ is defined as herein above excluding halo, and m is the integer 1 or 2.

A fuller and more complete understanding of the invention may be had from the following non-limiting Examples.

EXAMPLE I

2-(N-Succinimidyl)-4-pentyne

The compound 2(N-succinimidyl)-4-pentyne was prepared according to the method of Mitsunobu, M. Wada and T. Sano, J.A.C.S., 94, 679, (1972). 1.0 equivalent of diethylazodicarboxylate (4.7 ml) was added dropwise to a stirred ice cooled solution of 4-pentyn-2-ol (3 gm), triphenylphosphine (7.9 gm), and succinimide (3.6 gm) in 75 ml of dry tetrahydrofuran. The reaction mixture was allowed to reach room temperature and was left standing overnight. The reaction mixture was then concentrated in vacuo and the residue taken up in 300 ml of 30% ethyl acetate/petroleum ether. Upon concentration, an oily residue was obtained which, after fractional distillation, gave 2.0 gm of 2-(N-succinimidyl)-4-pentyne, bp 80°–84° C., 0.15 mm Hg. IR (neat): 1700, 1770, 2118 cm$^{-1}$. 'HNMR ($\delta$ CDCl$_3$): 1.4 (d, 3H, J=7.5 Hz, CH$_3$), 1.97 (t, 1H, J=2.6 Hz, —C≡C—H), 2.4–3.1 (m, 6H, CH$_2$), 4.1–4.7 ppm (m, 1H, CHN).

Compound 2-(N-succinimidyl)-4-hexyne was prepared in the same manner. 2-(N-succinimide)-4-hexyne: b.p. 100° C., 0.2 mm Hg; 'H NMR ($\delta$ CDCl$_3$): 1.4 (d, 3H, 7.2 Hz, CH$_3$), 1.73 (t, 3H, J=2.2 Hz, CH$_3$C≡C), 2.4–3.0 (m, 6H), 2.67 (s, —CH$_2$CH$_2$—), 4.1–4.6 (m, 1H, CHN). Threo-2-(N-succinimidyl)-3-methyl-4-pentyne was prepared from trans-2,3-epoxybutane and lithium acetylide as reported by Meinwald et al., J.A.C.S., 5364, 1979: 'H NMR ($\delta$CDCl$_3$): 1.27, 1.37 (2 d, 6H, J=6.7 Hz, CH$_3$), 1.97 (d, 1H, J=2.2 Hz, HC≡C, 2.27 (s, 4H, CH$_2$), 3.0–3.5 (m, 1H, HC(CH$_3$) C≡C), 4.0–4.5 ppm (m, 1H, J$_{vic}$=11.5 Hz, CHN). Erythro-2-(N-succinimidyl)-3-methyl-4-pentyne was obtained from a mixture of cis,-trans-2,3-epoxybutanes and lithium acetylide after separation from the threo isomer by HPLC (reverse phase chromatography eluting with 40% MeOH H$_2$O). 'H NMR ($\delta$CDCl$_3$): 1.05 (d, 3H, J=6.8 Hz, HC(CH$_3$) C≡C), 1.54 (d, 3H, J=6.9 Hz, NCH(CH$_3$)), 2.7 (s, 4H, CH$_2$), 3.0–3.5 (m, 1H, CH—C≡C), 4.1–4.6 ppm (m, 1H, J$_{vic}$=11.5 Hz, CHN).

EXAMPLE II

1-(4-pentyn-2-yl)-5-hydroxy-2-pyrrolidone

Following the method of A. R. Chamberlin and J. Y. L. Chung, Tet. Lett., 23, 2619, 1982(2), 3.0 equivalents of NaBH$_4$, 2.0 gm, were added portion-wise to 2-(N-succinimidyl)-4-pentyne (4.2 gm) in methanol (100 ml) with stirring at 0° C. Two hours after the addition, the reaction mixture was quenched with 100 ml of 5% NaHCO$_3$ and the methanol removed in vacuo. The resulting residue was diluted further in water and the aqueous portion extracted repeatedly with dichloromethane. The organic fractions were pooled, washed once with water, brine, and dried over anhydrous magnesium sulfate. Upon concentration 3.0 gm of an oily residue of 1-(4-pentyn-2-yl)-5-hydroxy-2-pyrrolidone was obtained. The two diastereomers could be separated on silica gel, eluting with ethyl acetate-petroleum ether. IR (neat): 3100-3600, 2118, 1640-1660 cm$^{-1}$. $^1$H NMR δ(CDCl$_3$, both diastereomers): 1.37, 1.42 (d, 3H, CH$_3$), 1.8-3.7 (m, 7H, CH$_2$, C≡C—H), 4.25 (m, 1H, CHN), 5.4 (app.t, 1H, HCOH(NR)). Alternatively, the reduction can be accomplished with 0.55 equivalents of RED-AL (sodium bis(2-methoxyethoxy)aluminum hydride) in toluene at −78° C. for two hours. Unreacted hydride is then destroyed with methanol and after treatment of the resulting mixture with Rochelle's salt, extraction with dichloromethane, drying and concentration of the organic extract, a high yield of product is obtained.

Compounds 1-(4-hexyn-2-yl)-5-hydroxy-2-pyrrolidone and erythro- and threo-1-(3-methyl-4-pentyn-2-yl)-5-hydroxy-2-pyrrolidone were made in the same manner.

EXAMPLE III

5-(1,2-Propadien-1-yl)-2-pyrrolidone 1-(4-pentyn-2-yl)-5-hydroxy-2-pyrrolidone (1.0 gm) was taken in (10 ml) of 95-97% formic acid at room temperature under argon and left standing for several days (three to five). The formic acid was then removed in vacuo and 5-(1,2-propadien-1-yl)-2-pyrrolidone was obtained pure by chromatography on silica gel, eluting with ethyl acetate. IR (neat): 3100-3600, 1955, 1670-1690 cm$^{-1}$, $^1$H NMR (δ CDCl$_3$): 2.0-2.5 (m, 4H, CH$_2$CH$_2$), 4.1-4.35 (m, 1H, CHN), 4.8-4.95 (m, 2H, CH$_2$=C=C), 5.05-5.25 (m, 1H, HC=C=C), 4.9 ppm (broad, NH).

Proceeding in the same manner, 5-(1,2-butadien-1-yl)-2-pyrrolidone and 5-(1-methyl-1,2-propadien-1-yl)2-pyrrolidone were prepared.

In the former case, threo-1-(3-methyl-4-pentyn-2-yl)-5-hydroxy-2-pyrrolidone gave mainly (8:2 ratio) of the (S,S) and (R,R) diastereomer 5-(1,2-butadiene-1-yl)-2-pyrrolidone, whereas erythrio-1-(3-methyl-4-pentyn-2-yl)-5-hydroxy-2-pyrrolidone gave only the (R,S) and (S,R) diastereomer. The diastereomers have identical $^1$H and $^{13}$C NMR resonances and only in the presence of Eu(fod)$_3$ are the allenic methyl signals different. IR (neat): 1958 cm$^{-1}$ (C=C=C); $^1$H NMR (δ CDCl$_3$): 1.6-2.8 (dd, 3H, J=3.3, 7.0 Hz, CH$_3$CH=C), 1.8-2.5 (m, 4H, CH$_2$), 4.0-4.3 (m, 1H, CHN), 5.0-5.5 (m, 2H, HC=C=CH), 5.6-6.1 ppm (broad s, 1H, NH). $^{13}$C NMR (δCDCl$_3$): 14.1 (q, CH$_3$), 28.2 (t, CH$_2$), 29.5 (t, CH$_2$), 53.42 (d, CHN), 89.1 (d, HC=C=C), 92.7 (d, HC=C=C), 178.2 (s, CO$_2$), 203.6 (s, C=C=C).

Alternatively, the arrangement of 1-(4-pentyn-2-yl)-5-hydroxy-2-pyrrolidone can be carried out more effectively in 20% CF$_3$CO$_2$H—CH$_2$Cl$_2$ at 5° for 5 days. The reaction mixture is then neutralized with saturated Na$_2$CO$_3$ and the aqueous portion extracted repeatedly with dichloromethane. The combined organic extracts are washed once with water, brine, dried over anhydrous MgSO$_4$ and concentrated in vacuo to an oil.

EXAMPLE IV

4-amino-5,6-heptadienoic acid 5-(1,2-Propadien-1-yl)-2-pyrrolidone (3.0 gm) was heated to 80° C. in 30 ml of 20% HCl under argon with stirring. After 2 days, the reaction mixture was diluted with water and extracted with ether. The pH of the aqueous portion was adjusted to 3.0 with 1.0N NaOH, and the sample introduced in an ion-exchange column Ag 50W×8 was eluted with 20% pyridine-water. Upon concentration of the eluant, a residue was obtained and 4-amino-5,6-heptadienoic acid was crystallized from acetone-water. mp 171° C. IR (KBr): 1957 cm$^{-1}$. $^1$H NMR (δ D$_2$O): 1.9-2.5 (m, 4H, —CH$_2$), 3.7-4.0 (m, 1H, —CHN), 5.1 (app. dd, 2H, H$_2$C=C=C), 5.3 ppm-(app. t, 1H, HC=C=C). $^{13}$C NMR (δ D$_2$O): 210 (s, C=C=C), 183.9 (s, CO$_2$), 90.5 (d, HC=C=), 82.0 (t, H$_2$C=C=C), 52.5 (d, —CHN), 36.1 (t, CH$_2$), 32.0 ppm (t, CH$_2$). Anal. Calcd. for C$_{17}$H$_{11}$NO$_2$H$_2$O: C, 52.82; H 8.23; N 8.80; Found: C, 52.67; H, 8.07; N, 8.79.

The compound 4-amino-5-methyl-5,6-heptadienoic acid was also prepared using this method.

The compounds 4-amino-5,6-octadienoic acids (both diastereomers) were also prepared using the above method. IR (KBr): 1965 cm$^{-1}$; $^1$H NMR (δD$_2$O): 1.7 (dd, 3H, J=3.3, 7.1 Hz, CH$_3$), 1.7-2.4 (m, 4H, CH$_2$), 3.6-3.9 (m, 1H, CHN), 5.1-5.7 (m, 2H, CH=C=CH); $^{13}$C NMR (δD$_2$O): 16.0 (CH$_3$), 32.06 (CH$_2$CHN), 36.11 (CH$_2$CO$_2$H), 52.74, 52.97 (CHN), 90.69 (CH$_3$CH), 93.93, 94.08 (CH CHN), 184.04 (CO$_2$H), 206.78 (C=C=C).

EXAMPLE V

1,5-Diacetyl-2-pyrrolidone

Following the method of W. Steglich, et al., Liebigs, Ann. Chem., 1753, 1974, (21.0 gm) of glutamic acid in 75 ml of acetic anhydride, 150 mg of 4-dimethylaminopyridine, and 75 ml of triethylamine was heated 60° C. overnight. The reaction mixture was then concentrated in vacuo, the residue taken up in dichloromethane and washed with water. The organic portion was treated with charcoal, filtered, concentrated and 1,5-diacetyl-2-pyrroidone was obtained crystalline from ether-dichloromethane, mp 62° C. $^1$H NMR (δ CDCl$_3$): 1.8-2.8 (m, CH$_2$), 2.3 (s, 3H, CH$_3$), 2.55 (s, 3H, CH$_3$), 4.8-5.0 ppm (dd, 1H, CHN).

EXAMPLE VI

5-(1-Acetoxy-1-methylprop-2-yn-1-yl)-2-pyrrolidone

Under dry and oxygen free conditions, 4.1 ml of 1.6M n-butyl lithium was added to 0.84 ml trimethylsilylacetylene at −78° C. in 30 ml of dry tetrahydrofuran. After 20 minutes, 1.0 gm of 1,5-diacetyl-2-pyrrolidone was added to the reaction mixture dropwise in tetrahydrofuran. The reaction mixture was then allowed to warm-up to room temperature over a 1½-2 hour period. A 1.0M solution of sodium hydroxide was then added and the reaction mixture was left standing for another 3 hours. The reaction mixture was then neutralized with 5% HCl at 0° C. and, after dilution with water, it was extracted repeatedly with chloroform. The chloroform fractions were pooled, washed once with water, brine, and dried over anhydrous magnesium sulfate. On concentrating, 5-(1-hydroxy-1-methylprop-2-yn-1-yl)-2-pyrrolidone was obtained as an oil. $^1$H NMR ($\delta$ CD$_3$OD): 1.45 (s, 3H, CH$_3$), 2.0–2.5 (m, 5H, CH$_2$, C≡CH), 3.65–3.85 (m, H, CHN).

The resulting oil was next taken to 80° C. in 1.85 ml of acetic anhydride and 10 ml of pyridine for 24 hours. The reaction mixture was then concentrated in vacuo, dissolved in chloroform and washed with water, 5% Na$_2$CO$_3$, and brine. The chloroform portion was next dried over anhydrous magnesium sulfate and concentrated to give an oil which crystallized from ether-dichloromethane giving 5-(1-acetoxy-1-methylprop-2-yn-1-yl)-2-pyrrolidone as an approximate 6:4 ratio of diastereomers. $^1$H NMR ($\delta$ CDCl$_3$): 1.6 (s, 3H, CH$_3$), 2.0 (s, 3H, CH$_3$CO), 2.1–2.7 (m, 5H, CH$_2$, C≡CH), 3.75–4.0 (m, 1H, CHN), 7.0 (broad d, 1H, NH).

EXAMPLE VII

5-(1-methyl-1,2-propadien-1-yl)-2-pyrrolidone

Lithium dimethylcuprate was prepared in the following manner: Cuprous iodide (Baker Grade); 2.03 gm was washed with 10 ml of dry tetrahydrofuran in the reaction flask. The tetrahydrofuran was then removed by syringe and finally by blowing with argon. The dry solid residue was then suspended in 20 ml of dry diethyl ether. AT −20° C., 15.3 ml of methyl lithium was added dropwise to give a yellow suspension which turned into a homogeneous dull yellow solution. The reaction mixture was then cooled to −78° and 260 mg of 5-(1-acetoxy-1-methylprop-2-yn-1-yl)-2-pyrrolidone in 4 ml of dry tetrahydrofuran was added dropwise to an excess (8.0 equivalents) of the lithium dimethylcuprate solution. The reaction mixture was stirred for an additional, 3 hours after which 5 ml of methanol were added at −78° C. After 5 min., 40 ml of a saturated solution of NH$_4$Cl was added, followed by 30 ml of a 0.8M solution of NH$_4$OH. The reaction mixture was brought to room temperature and the aqueous portion repeatedly extracted with chloroform. The combined organic fractions were washed once with water, brine, and dried over anhydrous magnesium sulfate. On concentrating, an oily residue was obtained consisting of 5-(1-methyl-1,2-propadien-1-yl)-2-pyrrolidone, and 5-(1-methyl-1,2-butadien-1-yl)-2-pyrrolidone, in a 4:1 ratio. Compound 5-(1-methyl-1,2-propadien-1-yl)-2-pyrrolidone was separated from 5-(methyl-1,2-butadien-1-yl)-2-pyrrolidone by HPLC (RP-18, 50% methanol-water). 5-(1-methyl-1,2-propadien-1-yl)-2-pyrrolidone had: IR (neat), 3100–3400, 1951, 1670 cm$^{-1}$, $^1$H NMR ($\delta$ CDCl$_3$): 1.7 (app.t, 3H, CH$_3$), 1.9–2.5 (m, 4H, CH$_2$), 4.0–4.2 (m, 1H, CHN), 4.7–4.9 (m, 2H, H$_2$C=C=C), 5.8 (broad, 1H, NH). 5-(1-methyl-1,2-butadien-1-yl)-2-pyrrolidone: IR (neat): 1950, 1680 cm$^{-1}$, $^1$H NMR ($\delta$ CDCl$_3$): 1.55–1.7 (m, 6H, CH$_3$), 1.8–2.5 (m, 4H, CH$_2$CH$_2$), 3.95–4.2 (m, 6H, CHN), 5.0–5.23 (m, 2H, HC=C=CH), 5.7 ppm (broad, 1H, NH), $^{13}$C NMR ($\delta$ CDCl$_3$ both diastereomers): 200.6 (C=C=C), 178.3 (CO), 99.7 (—C(CH$_3$)=C=CH(CH$_3$)), 87.8, 87.7)-C(CH$_3$)=C=CH(CH$_3$)), 14.8, 14.2 (CH$_3$C=C=CCH$_3$).

EXAMLE VIII

4-amino-5-methyl-5,6-heptadienoic acid

The compound 5-(methyl-1,2-propadien-1-yl)-2-pyrrolidone was converted to 4-amino-5-methyl-5,6-heptadienoic acid by heating 140 mg of the 5-(1-methyl-1,2-propadien-1-yl)-2-pyrrolidone at 80° C. in 10 ml of 20% HCl under argon with stirring for 2 days. After refluxing, the reaction mixture was concentrated and the sample applied on a short column of RP-18 material eluting with water. Upon lyophilization 4-amino-5-methyl-5,6-heptadienoic acid was obtained as a fluffy white material, mp 140° C. (dec), IR(KBr): 1958, 1640 cm$^{-1}$, $^1$H NMR ($\delta$D$_2$O): : 1.75 (app.t, 3H, CH$_3$), 1.9–2.45 (m, 4H, CH$_2$), 3.75–3.9 (m, 1H, CHN), 5.0(m, 2H, CH$_2$=C=C).

Using the processes of Examples V, VI, VII to prepare the precursors, and the foregoing reagents or appropriate variations thereof, and conditions of this Example, the following exemplary. compounds may be prepared:

4-amino-5-ethyl-5,6-heptadienoic acid;
4-amino-5-phenyl-5,6-heptadienoic acid;
4-amino-5-(4-chlorophenyl)-5,6-heptadienoic acid;
4-amino-5-phenylpropyl-5,6-heptadienoic acid;
4-amino-5,7-dimethyl-5,6-heptadienoic acid;
4-amino-5-butyl-5,6-heptadienoic acid;
4-amino-5-methyl-5,6-octadienoic acid;
4-amino-5-butyl-5,6-octadienoic acid;
5-amino-6-methyl-6,7-dodecadienoic acid;
5-amino-6,8-dimethyl-6,7-dodecadienoic acid;
5-amino-6-butyl-6,7-dodecadienoic acid;
5-amino-6,7-dodecadienoic acid; and
5-amino-6,8-dibutyl-6,7-dodecadienoic acid.

EXAMPLE IX

Octyl 4-amino-5,6-heptadienoate para-toluene sulfonic acid salt

In 10 ml of benzene, 60 mg of 4-amino-5,6-heptadienoic acid, 1 ml of octanol, and 100 mg of para-toluene sulfonic acid were refluxed in a Dean-Stark apparatus for 2 days. Benzene and excess octanol were removed in vacuo, the resulting residue was taken up in acetone and filtered. The filtrate was concentrated and ether added. Octyl 4-amino-5,6-heptadienoate para-toluene sulfonic acid salt crystallized out of solution: mp 87°–88° C., IR (KBr) 2500–3300, 1957, 1725 cm$^{-1}$, $^1$H NMR ($\delta$-CDCl$_3$): 0.8–2.5 (m, 2=H), 2.37 (s, (CH$_3$Ph), 3.75 (m, 1H, CHN), 4.0 (t, 6.4 Hz, OCH$_2$), 4.8 (app. dd, 2H, H$_2$C=C=C), 5.15 (m, 1H, CH=C=C), 7.15 (d, 2H, CH$_3$PhSO$_3$—), 7.77 (d, 2H, CH$_3$PhSO$_3$—), 8.05 ppm (broad, 3H, NH, OH) Anal. calcd. for C$_{22}$H$_{35}$NO$_5$S; C, 61.77; H, 8.03; N, 3.15; S, 7.7; Found: C, 62.09; H, 8.29; N, 3.29; S, 7.53.

The ethyl ester was made in the same way: mp 73°–74° C., IR (KBr): 2500–3300, 1958, 1723 cm$^{-1}$, $^1$H NMR ($\delta$CDCl$_3$): 1.2 (t, 3H, 7.2 Hz, CH$_3$), 1.8–2.5 (m, 7H), 2.37 (s, CH$_3$Ph), 3.73 (m, 1H, CHN), 4.07 (g, 2H, J=7.2 Hz, OCH$_2$), 4.8 (app. dd, 2H, H$_2$C=C=C), 5.17 (m, 1H, HC=C=C), 7.15 (d, 2H, CH$_2$PhSO$_3$), 7.87 (d, 2H, CH$_3$PhSO$_3$—), 8.05 (broad, 3H, NH, OH). Anal. calcd. for C$_{22}$H$_{35}$NO$_5$S; C, 61.77; H, 8.03; N, 3.15; S, 7.7; Found: C, 62.09; H, 8.29; N, 3.29; S, 7.53.

In the same manner, octyl-4-amino-5-methyl-5,6-heptadienoate para-toluene-sulfonic acid salt was made. mp. 62° C., IR (KBr): 1760, 1725 cm$^{-1}$; $^1$H NMR ($\delta$CDCl$_3$): 0.8–2.5 (m, 21H), 2.37 (s, 3H, CH$_3$Ph), 3.7 (m, 1H, CHN), 4.0 (t, 2H, J=6.7 Hz, OCH$_2$), 4.9 (m, 2H, H$_2$C=C), 7.15, 7.77 (d, 4H, Ph), 7.25 (broad s, 3H, NH, OH).

EXAMPLE X

4-N-tert-butyloxycarbonyl-5,6-heptadienoic acid

The title compound was prepared according to the procedure of M. Toh, D. Hagiwara and T. Kamiya, Tett. Lett. 4393, 1975. mp 73°–73° C., $^1$H NMR ($\delta$CDCl$_3$): 1.47 (s, 9H, t-butyl), 1.65–2.1 (m, 2H, CH$_2$), 2.45 (app.t, 2H, CH$_2$CO), 4.2 (m, 1H, NH), 4.65 (m, 1H, CHN), 4.9 (m, 2H, CH$_2$C=C=C), 5.2 (m, 1H, HC=C=C), 10–11 ppm (broad, 1H, OH).

EXAMPLE XI

N-Benzyloxymethylene-5-carbomethoxy-2-pyrrolidone

5-Carbomethoxy-2-pyrrolidone, prepared from pyroglutamic acid, thionyl chloride and methanol according to the method of S. Shigeyoshi, et al., Chem. Pharm. Bull., 1980, 28 (5), 1449, was added dropwise in dry THF to a slurry of 1.1 equivalent of KH in THF at 0° C. Two hours after the addition 1:1 equivalent of chloromethyl benzyl ether was added dropwise at 0° C. and then left for 24 hours at room temperature. A 5% NaHCO$_3$ solution was then added and the resulting mixture extracted repeatedly with ethyl acetate. The organic extract was washed once with water, brine and then dried over anh. MgSO$_4$. Concentration in vacuo gave an oily residue which on purification by chromatography on silica gel, eluting with ethyl acetate-petroleum ether gave the desired product. IR (neat): 1740, 1705 cm$^{-1}$. $^1$H NMR ($\delta$CDCl$_3$): 2.9–3.6 (m, 4H, CH$_2$CH$_2$), 3.72 (s, 3H, OCH$_3$), 4.5 (AB, 2H, J=12 Hz, CH$_2$Ph), 4.7 (m, 1H, CHN), 4.9 (AB, 2H, J=12 Hz, NCH$_2$O), 7.35 (s, 5H, Ph).

EXAMPLE XII

N-Benzyloxymethylene-5-formyl-2-pyrrolidone

To N-benzyloxymethylene-5-carbomethoxy-2-pyrrolidone in ethanol at 0° C. was added portion-wise 5.0 equivalents of NaBH. After the addition, the reaction mixture was left stirring overnight at room temperature. It was then treated with 10% HCl to destroy excess hydride, followed by 5% NaHCO$_3$. The resulting mixture was evaporated in a rotary evaporator to remove the bulk of the ethanol and then repeatedly extracted with dichloromethane. The combined organic fractions were washed with brine, dried over anh. MgSO$_4$ and concentrated to a viscous oil. The product; N-benzyloxymethylene-5-hydroxymethyl-2-pyrrolidone was then oxidized to the title compound with DMSO by following the method of Swern et al, JOC 43, 2480, 1978. Hence 4.2 ml of DMSO in 10 ml of dry dichloromethane was added to a −70° C. dichloromethane solution containing 2.6 ml of oxalyl chloride. 6.0 gm of N-benzyloxymethylene-5-hydroxymethyl-2-pyrrolidone in 20 ml of dry CH$_2$Cl$_2$ was added dropwise and after 5 min., 18.6 ml of NEt$_3$. The reaction mixture was warmed to room temperature and 200 ml of water was added. Repeated extraction with CH$_2$Cl$_2$, washing of the combined organic fractions with water, brine, drying over anh. MgSO$_4$ and concentration gave a dark oil. Purification by chromatography on SiO$_2$ gave 3.0 gm of N-benzyloxymethylene-5-formyl-2-pyrrolidone. IR: 1700–1710 cm$^{-1}$; $^1$H NMR ($\delta$CDCl$_3$): 1.9–2.5 (m, 4H, CH$_2$CH$_2$), 4.2–4.4 (m, 1H, CHN), 4.55 (AB, 2H, J=12 Hz, CH$_2$Ph), 4.9 (AB, 2H, J=12 hz, NCH$_2$O), 7.35 (s, 5H, Ph), 9.6 (d, 1H, J=2.2 Hz).

EXAMPLE XIII

N-Benzyloxymethylene-5-(1-hydroxyprop-2-yn-1-yl)-2-pyrrolidone

The title compound was prepared as described in Example VI. Hence, 3.0 ml of a 1.65M solution of n-butyl lithium in hexane was added to 15 ml of a THF solution containing 0.7 ml of trimethylsilyl acetylene at −40° C. with stirring and under nitrogen. After 20 min. the reaction vessel was cooled to −70° C. and 0.97 gm of N-benzyloxymethylene-5-formyl-2-pyrrolidone in 2 ml of THF was added dropwise. After 1 hour, the reaction mixture was warmed to −40° C. and after another hour 10 ml of a 1.0M NaOH was added. The reaction mixture was then left stirring at room temperature overnight. 30 ml of water was added and the aqueous portion extracted with 4×50 ml of ether. The ether extracts were combined, washed with brine, dried over anh. MgSO$_4$, and concentrated to give a 3:2 ratio of diastereomers of N-benzyloxymethylene-5-(1-hydroxyprop-2-yn-1-yl)-2-pyrrolidone as a light yellow oil. IR (neat): 3100–3000, 3300, 2120, 1700 cm$^{-1}$. $^1$H NMR ($\delta$CDCL$_3$), 2.9–3.7 (m, 5H, CH$_2$CH$_2$, OH), 2.5 (d, 1H, J=2.2 Hz, C≡CH), 3.7–4.0 (m, 1H, CHN), 4.4–5.4 (m, 5H, NCH$_2$OCH$_2$CHOH), 7.35 (s, 5H, Ph). $^{13}$C NMR ($\delta$CDCL$_3$): 19.4, 20.0 (CH$_2$CHN), 29.6, 29.7 (CH$_2$CO), 62.1–63.1 (CHN), 63.6, 63.7 (CHO), 70.72, 70.78, 71.53, 71.87, 74.0, 74.3, 81.35, 81.85. (NCH$_2$OCH$_2$, CH≡C), 127.4, 127.5, 127.7, 128 (Ph), 136.7, 137.1 (Ph), 176.9, 177.2 ppm (CO).

EXAMPLE XIV

N-Benzyloxymethylene-5-(3-bromo-1,2-propadien-1-yl)-2-pyrrolidone

Following the procedure of Vermeer, JOC 47, 2194, 1982, 1.35 g of N-benzyloxymethylene-5-(1-hydroxyprop-2-yn-1-yl)-2-pyrrolidone in 20 ml of dry THF at −70° C. was treated with a 1.65 ml n-butyl lithium hexane solution. A precipitate formed and 15 min. after the addition, 1.05 gm of LiCuBr$_2$ in 10 ml of THF (prepared from 2.1 gm of CuBr and 0.64 gm of LiBr). The resulting mixture was left at −70° C. for 1 hour and then it was slowly warmed to room temperature and left for 16 hours. The reaction mixture was then quenched with 100 ml of saturated NH$_4$Cl and extracted with 5×50 ml of ether. The combined ether extracts were washed once with brine, dried over anh. MgSO$_4$, and concentrated to an oil. Purification by chromatography on SiO$_2$ gave the title compound as a mixture of diasteromers. IR (neat): 1958, 1700 cm$^{-1}$. $^1$H NMR ($\delta$CDCl$_3$): 1.8–2.7 (m, 4H, CH$_2$CH$_2$), 4.35 (m, 1H, CHN), 4.6 (AB, 2H, CH$_2$Ph), 4.95 (AB, 2H, J=12 Hz, NCH$_2$O), 5.35 (dd, 1H, J=6.5, 6.0 Hz, HC=C), 6.1 (m, 1H, HC(Br)=C), 7.35 ppm (s, 5H, Ph).

N-Benzyloxymethylene-5-(3-chloro-1,2-propadien-1-yl)-2-pyrrolidone was made in a similar way by using LiCuCl$_2$. IR (neat): 1960, 1700 cm$^{-1}$; $^1$H NMR ($\delta$CDCl$_3$): 1.9–2.6 (m, 4H, CH$_2$CH$_2$), 4.4 (m, 1H, CHN), 4.6, 4.9 (2AB, 4H, NCH$_2$OCH$_2$Ph), 5.6 (app t, 1H, J=6.0 Hz, HC=C=C), 6.17 (m, 1H, HC(Cl)=C), 7.35 ppm (s, 5H, Ph).

EXAMPLE XV

4-Amino-7-bromo-5,6-heptadienoic acid

N-Benzyloxymethylene-5-(3-bromo-1,2-propadien-1-yl)-2-pyrrolidone was refluxed in 1:1 THF: 20% HCl for 2 days under argon. The reaction mixture was diluted with water, extracted with ether, and ion-exchange chromatography performed (Ag 50 W×8) eluting with 20% pyridine water. Upon concentration, the resulting residue was applied on a reverse phase HPLC (RP-18) column yielding the title compound as a mixture of diastereomers after lyophilization of the appropriate fraction. IR (KBr): 1962(w), 1660(m), 1540(s), 1390(s) cm$^{-1}$. $^1$H NMR ($\delta$D$_2$): 1.9–2.5 (m, 4H, CH$_2$CH$_2$), 4.05 (m, 1H, CHN), 5.65 (t, 1H, J=6.0 Hz, HC=C), 6.55 (app dd, 1H, HC(Br)=C). $^{13}$C NMR ($\delta$D$_2$O): 31.6, 31.8 (CH$_2$CHN), 36.0 (CH$_2$CO), 51.7, 51.8 (CHN), 79.4 (CH=C), 99.6, 99.8 (HC=C), 183.6 (CO$_2$), 204.2, 204.4 (C=C=C).

4-Amino-7-chloro-5,6-heptadienoic acid was made in the same manner. IR (KBr): 1965, 1575 cm$^{-1}$; $^1$H NMR ($\delta$D$_2$O): 1.9–2.5 (m, 4H, CH$_2$CH$_2$), 4.05 (m, 1H, CHN), 5.95 (app t, 1H, J=6 Hz, HC=C), 6.62 (app dd, 1H, HC(Cl)=C). $^{13}$C NMR ($\delta$D$_2$O): 31.7 (CH$_2$CHN), 36.0 (CH$_2$CO), 52.3 (CHN), 95.8 (HC=C), 101.38, 101.51 (HC(Cl)=C), 183.7 (CO$_2$), 204.6, 204.8 (C=C=C).

EXAMPLE XVI

Ethyl 4-amino-5,6-heptadienoate hydrochloride salt

To 4-amino-5,6-heptadienoic acid in anhydrous ethanol at 0° C. was added gaseous HCl. The reaction was left overnight at room temperature and then evacuated to a residue. This was taken in ethyl acetate, decolorized with charcoal, and then crystallization accomplished from ethyl acetate-ether to give the title compound. mp. 81°–83° C.; IR (KBr): 1952, 1710 cm$^{-1}$. $^1$H NMR ($\delta$D$_2$O): 1.3 (t, 3H, J=6.9 Hz, CH$_3$), 1.9–2.8 (m, 4H, CH$_2$CH$_2$), 3.95 (m, 1H, CHN), 4.2 (q, 2H, J=6.9 Hz, OCH$_2$), 5.0–5.4 (m, 3H H$_2$C=C=CH). Anal. Calcd. for C$_9$H$_{16}$ClNO$_2$: C, 52.56, H, 7.84, N, 6.87; Found: C, 52.45, H, 7.95, N, 6.98.

EXAMPLE XVII

4-Amino-5-methyl-7-chloro-5,6-heptadienoic acid

To a toluene solution of 5-(1-hydroxy-1-methylprop-2-yn-1-yl)-2-pyrrolidone at room temperature was added 4.0 equivalents of pyridine and 1.5 equivalents of thionyl chloride. The reaction mixture was left for four days. It was then quenched with cold water, extracted repeatedly with ethyl acetate and the organic extract washed once with water, brine, dried over anh. MgSO$_4$ and concentrated to give an oil. Purification by chromatography over silica gel gave a 1:1 ratio of 5-(1-methyl-3-chloro-1,2-propadien-1-yl)-2-pyrrolidone (IR 1960 cm$^{-1}$) and 5-(1-methyleneprop-2-yne-1-yl)-2-pyrrolidone (IR 2100 cm$^{-1}$). The mixture was then refluxed in a 1:1 solution of THF: 20% HCl for 2 days, diluted with water, and washed with ether. The aqueous phase was passed through an ion-exchange column (Ag 50 W×8) eluting with 20% pyridine-water. The concentrate was then chromatographed on HPLC (RP-18) giving two diasteromeric allenes which separated under the HPLC conditions. 4-Amino-5-methyl-7-chloro-5,6-heptadienoic acid; IR (KBr): 1962, 1545 cm$^{-1}$, $^1$H NMR ($\delta$D$_2$O): 1.93 (d, 3H, J=2.2 Hz, CH$_3$), 1.9–2.5 (m, 4H, CH$_2$CH$_2$), 3.9 (m, 1H, CHN), 6.49 (m, 1H, CH=C), mass spectrum (M+Cl 154), 102, 84; and 4-amino-5-methylene-6-heptynoic acid IR: 3165, 2130, 1610, 1540 cm$^{-1}$; $^1$H NMR ($\delta$D$_2$O): 1.9–2.5 (m-4H, CH$_2$CH$_2$), 2.58 (s, 1H, C=CH), 2.96 (m, 1H, HCN), 5.8 (d, 2H, J=7.3 Hz, H$_2$C=C).

EXAMPLE XVIII

Trans-4-amino-2,5,6-heptatrienoic acid

To ethyl 4-amino-5,6-heptadienoate hydrochloride in chloroform containing one equivalent of NEt$_3$, was added 1.0 equivalent of di-tert-butyl-dicarbonate at 0° C. The reaction mixture was then warmed to room temperature and left overnight. Dilution with chloroform was followed by washing with water, brine, drying over anh. MgSO$_4$, and concentration in vacuo to give ethyl-4-N-tert-butoxycarbonyl-5,6-heptadienoate as an oil. This was added in dry THF to an LDA solution (2.2 equivalents) at $-70°$ C., dropwise, and under argon. One hour after the addition, 1.0 equivalents of phenylselenium bromide was added according to the method of Sharpless et al, JACS, 6137, 1973. After 1 hour the reaction mixture was warmed to 0° C. and quenched with 10% acetic acid and extracted repeatedly with CH$_2$Cl$_2$. The organic fractions were combined, washed with 5% NaHCO$_3$, brine, dried over anh. MgSO$_4$ and concentrated to an oil. Partial purification by chromatography on SiO$_2$ gave three allene products; starting material, ethyl-4-N-tert-butoxycarbonyl-2-phenylselenyl-5,6-heptadienoate, and N-tert-butoxycarbonyl-5-(1,2-propadien-1-yl)-3-phenylselenyl-2-pyrrolidone. The allene samples were dissolved in methanol and treated with 3.0 equivalents of NaIO$_4$ at room temperature overnight. The reaction mixture was then concentrated, diluted with water and extracted repeatedly with CH$_2$Cl$_2$ to give after drying over anh. MgSO$_4$ and concentration, an oil consisting of cis- and trans-ethyl-4-N-tert-butoxycarbonyl-2,5,6-trienoate. This was partially purified on SiO$_2$. The allene fractions were combined and treated with a 1:1 solution of THF: 20% HCl at reflux for two days. Water was added to the reaction mixture and the latter extracted with ether. Ion-exchange chromatography (Ag 50 W×8), eluting with 20% pyridine water gave a residue which on purification by HPLC (RP-18) gave trans-4-amino-2,5,6-heptatrienoic acid. $^1$H NMR ($\delta$D$_2$O): 4.5 (m, 1H, HCN), 5.1–5.3 (m, 2H, H$_2$C=C=C), 5.35–5.65 (m, 1H, CH=C=C), 6.1 (dd, 1H, J=0.65, 15.8 Hz, HC=C), 6.5 (dd, 1H, J=6.3, 15.8 Hz, HC=C); mass spectrum, m/e 100; MH$^+$ 140, (MH−H$_2$O 122), (MH±NH$_2$ 124), 100.

EXAMPLE IXX

ASSAY PROCEDURES

Mammalian $\gamma$-aminobutyric acid transaminase (GABA-T) was purified from pig brain by the procedure of Churchich and Moses (J. Biol. Chem., 256, 1101 (1981)). Bacterial succinic semialdehyde dehydrogenase (SSDH) was prepared by sodium borohydride inactivation of bacterial GABA-T in preparations of GABASE from *Pseudomonas fluorescens* (purchased from Sigma Chemical Co.).

Mammalian GABA-T was incubated with inhibitor (25 micromolar to 1 millimolar) at pH 8.6, 25° C. and 1 mM $\beta$-mercaptoehtanol in the presence or absence of different effectors such as 2-oxoglutarate, pyridoxal-P. At appropriate time intervals aliquots of the incubation mixture were withdrawn and residual GABA-T activity determined.

The residual activity measurements were determined by coupling the formation of succinic semialdehyde to SSDH-dependent reduction of NADP and following the formation of NADPH at 340 nm in a spectrophotometric cuvette using a modification of a method outlined by Sigma Chemical Co. for product No. B-7507. Bacterial GABASE. The cuvette contained the following medium: 100 mM pyrophosphate buffer pH 8.6; 6 mM γ-aminobutyrate; 5 mM 2-oxoglutarate; 3 mM β-meercaptoethanol; 1 mM NADP; and sufficient SSDH so that GABA-T activity was rate limiting.

EXAMPLE XX

C. ELEGANS ASSAY

The compounds tested were dissolved in DMSO at 10 mg/ml to give sample stock solutions. During assay, 1 ml M9 buffer (6 g $Na_2HPO_4$, 3 g $KH_2PO_4$, 5 g NaCl, and 0.25 g $MgSO_4\cdot H_2O$ per liter) was placed in each of the 24-wells in a tissue culture plate. 10 μl of sample stock solution was added respectively to each of 23 wells. The remaining well served as drug-free control.

At time 0, 1 drop of C. elegans suspension was dropped into each well (25–50 adults). At 1 hour, the number of active worms versus total in each well was recorded.

| Compound | % Active |
|---|---|
| Control | 100% |
| Octyl 4-amino-5,6-heptadienoate para-toluene sulfonic acid salt | 45% |
| Octyl 4-amino-5-methyl-5,6-heptanoate | 25 % |

EXAMPLE XXI

N. BRASILIENSIS ASSAY

The compound was tested at 50 μg/ml against the third larval stage of N. Brasiliensis at approximately 50 $L_3$/well; this mixture was incubated at 37° C. for total of 7 days. Activity of the compound was checked on days 1, 4. and 7 post-inoculation.

| Compound | Percent Viable |
|---|---|
| Control | day 1, 100% |
|  | day 4, 100% |
|  | day 7, 100% |
| Octyl 4-amino-5,6-heptadienoate para-toluene sulfonic acid salt | day 1, 64% |
|  | day 4, 0% |
|  | day 7, 0% |

EXAMPLE XXII

Toxicity Test of 4-amino-5,6-heptadienoic acid 4-amino-5,6-heptadienoic acid prepared in CMC vehicle was administered once daily to groups of 6 male mice at doses of 0, 62.5, 125, 250 and 500 mg/Kg. The animals were observed for 21 days and no deaths were noted in any of the dose groups. Therefore, the $LD_{50}$ (acute, oral, mouse) for 4-amino-5,6-heptadienoic acid is greater than 500 mg/Kg.

Other compounds of the invention exhibit similar toxicity.

What is claimed is:

1. A compound of the formula:

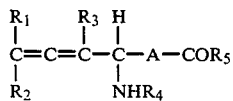

or a pharmaceutically acceptable salt thereof wherein:

$R_1$, $R_2$ and $R_3$ are independently selected from the group consisting of hydrogen; halo; and alkyl of 1 to 4 carbon atoms; provided that at least one of $R_1$, $R_2$ and $R_3$ is not hydrogen when A is $-CH_2-CH_2-$;

$R_4$ is hydrogen;

$R_5$ is hydroxyl or alkoxy of 1 to 22 carbon atoms;

A is $-CH=CH-$ or $-CH_2-CH_2-$.

2. A compound according to claim 1 wherein one of $R_1$, $R_2$ and $R_3$ is alkyl of 1 to 4 carbon atoms and $R_5$ is hydroxyl or alkoxy of 8 carbon atoms.

3. A compound according to claim 2 wherein $R_1$, $R_2$ and $R_3$ are independently hydrogen or methyl.

4. A comound according to claim 3 which is 4-amino-5-methyl-5,6-heptadienoic acid or a pharmaceutically acceptable salt thereof.

5. A compound according to claim 3 which is 4-amino-5,6-octadienoic acid or a pharmaceutically acceptable salt thereof.

6. A compound according to claim 3 which is octyl 4-amino-5-methyl-5,6-heptadienoate or its para-toluene-sulfonic acid salt.

7. A compound according to claim 1 wherein one of $R_1$ and $R_2$, is chloro, or bromo, $R_3$ is hydrogen, $R_5$ is hydroxyl, and A is 13 $CH_2-CH_2-$.

8. A compound according to claim 7 which is 4-amino-7-chloro-5,6-heptadienoic acid or a pharmaceutically acceptable salt thereof.

9. A compound according to claim 7 which is 4-amino-7-bromo-5,6-heptadienoic acid or a pharmaceutically acceptable salt thereof.

10. A compound according to claim 1 wherein $R_1$ and $R_2$ are independently hydrogen or halo, $R_3$ is alkyl of 1 to 4 carbon atoms, and A is $-CH_2-CH_2-$.

11. A compound according to claim 10 which is 4-amino-7-chloro-5-methyl-5,6-heptadienoic acid or a pharmaceutically acceptable salt thereof.

12. A compound according to claim 1 wherein $R_1$, $R_2$, $R_3$ and $R_4$ are all hydrogen, $R_5$ is hydroxyl and A is $-CH=CH-$, namely 4-amino-2,5,6-heptatrienoic acid or a pharmaceutically acceptable salt thereof.

13. A pharmaceutical composition comprising a compound of claim 1 or a pharmaceutically acceptable salt thereof alone or in admixture with a pharmaceutically acceptable excipient.

14. A method for treating parasitic infections in mammals, which method comprises administering to a mammal an effective amount of a compound of claim 1 or a pharmaceutically acceptable salt thereof either alone or in admixture with a pharmaceutical excipient.

15. A compound of the formula:

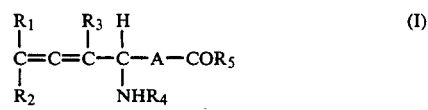

or a pharmaceutically acceptable salt thereof wherein:

$R_1$, $R_2$ and $R_3$ are independently selected from the group consisting of hydrogen; chloro; bromo; and alkyl of 1 to 4 carbon atoms; provided that at least one of $R_1$, $R_2$ and $R_3$ is not hydrogen when A is $-CH_2-CH_2-$;

$R_4$ is hydrogen;

$R_5$ is hydroxyl;

A is $-CH=CH-$ or $-CH_2-CH_2-$.

16. A compound of claim 15 wherein $R_1$ $R_2$ and $R_3$ are independently hydrogen, chloro, bromo, or methyl.

17. A compound of claim 15 wherein A is —CH$_2$—CH$_2$—.

18. A compound of claim 15 wherein A is —CH$_2$—CH$_2$—.

19. A pharmaceutical composition comprising a compound of claim 15 or a pharmaceutically acceptable salt thereof alone or in admixture with a pharmaceutically acceptable excipient.

20. A method for treating parasitic infections in mammals, which method comprises administering to a mammal an effective amount of a compound of claim 15 or a pharmaceutically acceptable salt thereof either alone or in admixture with a pharmaceutical excipient.

* * * * *